Figure 1:
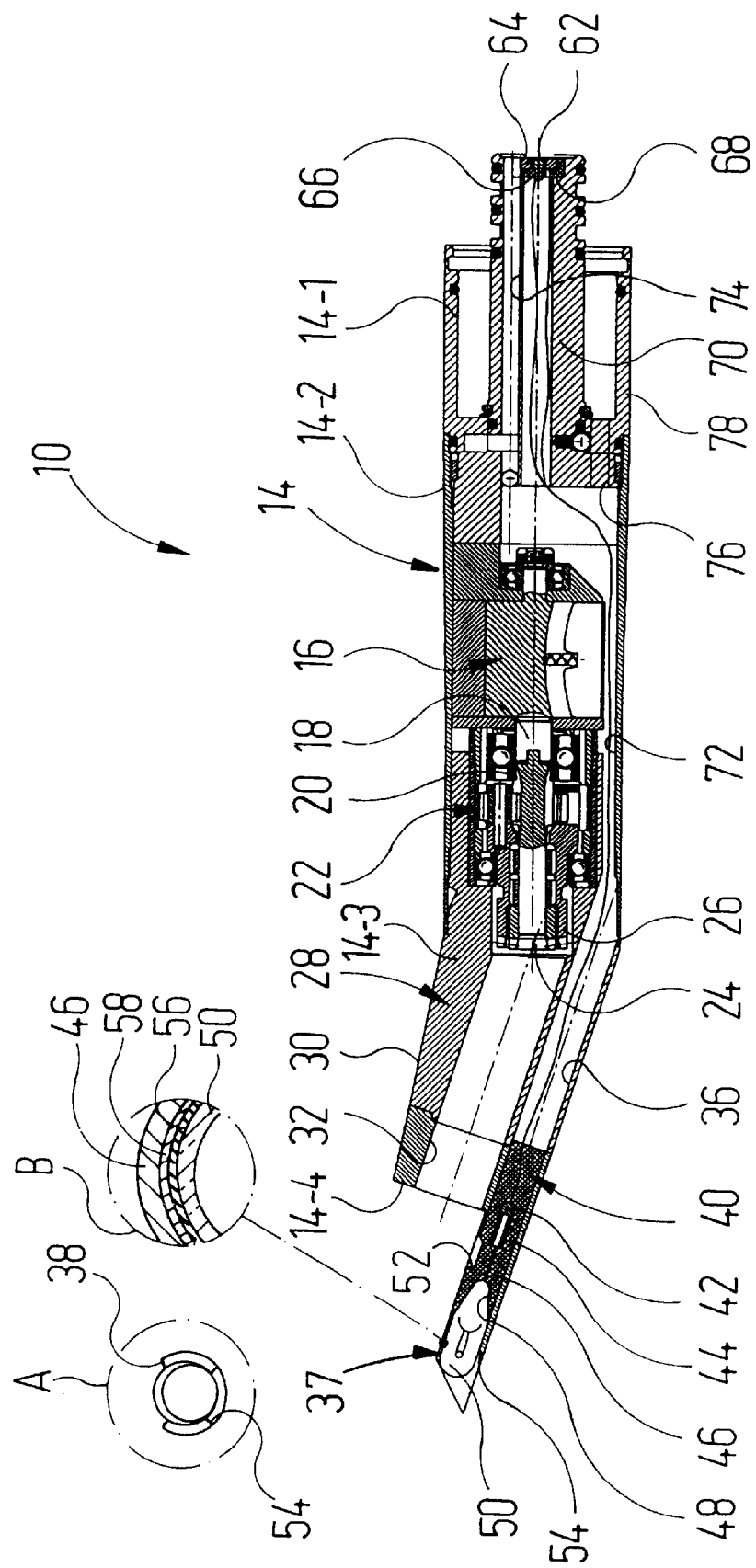

United States Patent [19]
Rosenstatter

[11] Patent Number: 6,161,937
[45] Date of Patent: Dec. 19, 2000

[54] DENTAL HANDPIECE

[76] Inventor: Otto Rosenstatter, Matzing 105, A-5164 Seeham, Austria

[21] Appl. No.: 08/998,526

[22] Filed: Dec. 26, 1997

[30] Foreign Application Priority Data

Dec. 29, 1996 [DE] Germany .......................... 196 54 400

[51] Int. Cl.$^7$ .................................................. F21V 33/00
[52] U.S. Cl. ......................... 362/109; 362/120; 362/804; 433/29
[58] Field of Search .................................... 362/109, 119, 362/120, 804; 433/29

[56] References Cited

U.S. PATENT DOCUMENTS

| | | | |
|---|---|---|---|
| 1,932,473 | 10/1933 | Morgan et al. | 362/804 X |
| 2,038,911 | 4/1936 | Stutz et al. | 362/119 |
| 2,226,616 | 12/1940 | Kraus | 362/119 |
| 2,289,226 | 7/1942 | Von Foregger | 362/119 X |
| 2,444,207 | 6/1948 | Smith | 362/804 X |
| 2,588,288 | 3/1952 | Pohanka | 362/119 X |
| 3,373,737 | 3/1968 | Moore et al. | 362/119 X |
| 3,614,414 | 10/1971 | Gores | 362/119 X |
| 4,642,738 | 2/1987 | Meller | 362/119 |
| 4,657,012 | 4/1987 | Burgin | 362/119 X |
| 4,785,796 | 11/1988 | Mattson | 362/109 X |
| 5,003,434 | 3/1991 | Gonser et al. | 362/119 X |
| 5,457,611 | 10/1995 | Verderber | 362/32 |

Primary Examiner—Thomas M. Sember
Assistant Examiner—John A. Ward

[57] ABSTRACT

A dental handpiece with integrated light source has on its casing a socket for a lamp carrier which in turn has a lamp socket. An incandescent lamp is inserted into said lamp socket. In those regions in which the incandescent lamp is covered up by the lamp carrier or parts of the casing a reflecting layer is provided on the outer surface of the incandescent lamp. This may be, for example, a metal film deposited by vaporisation onto the outer surface of the lamp in the appropriate region. The lamp carrier is molded onto the partially vapor-coated incandescent lamp.

33 Claims, 15 Drawing Sheets

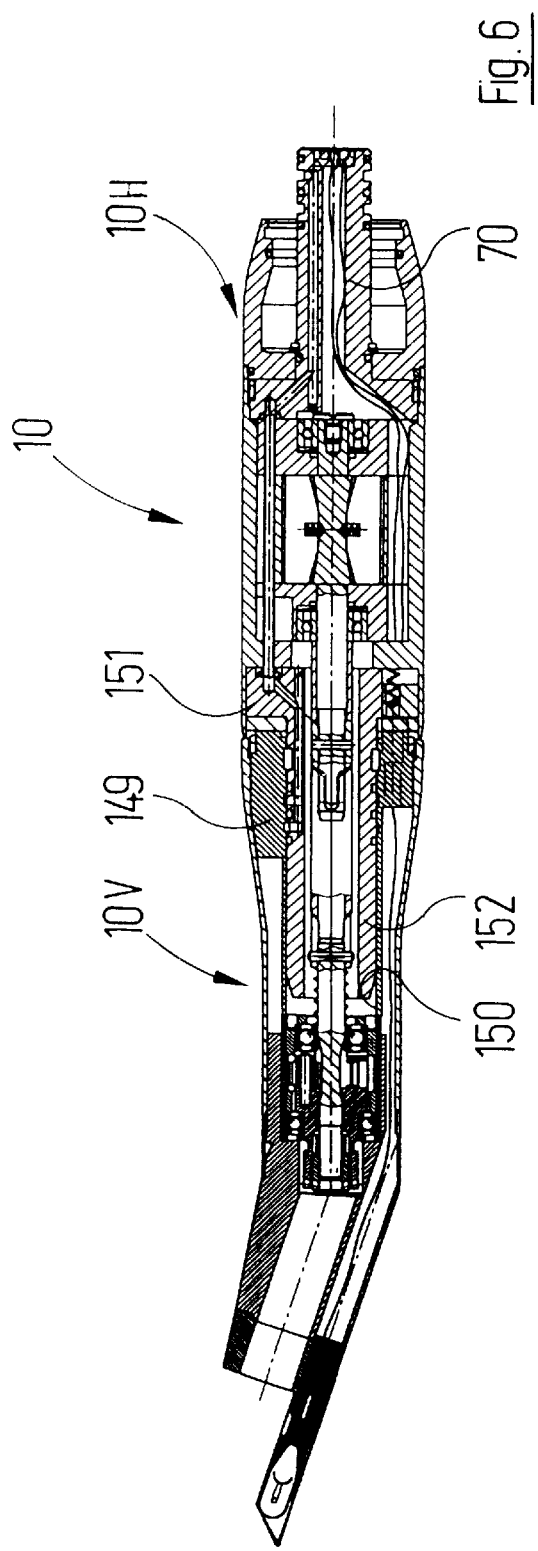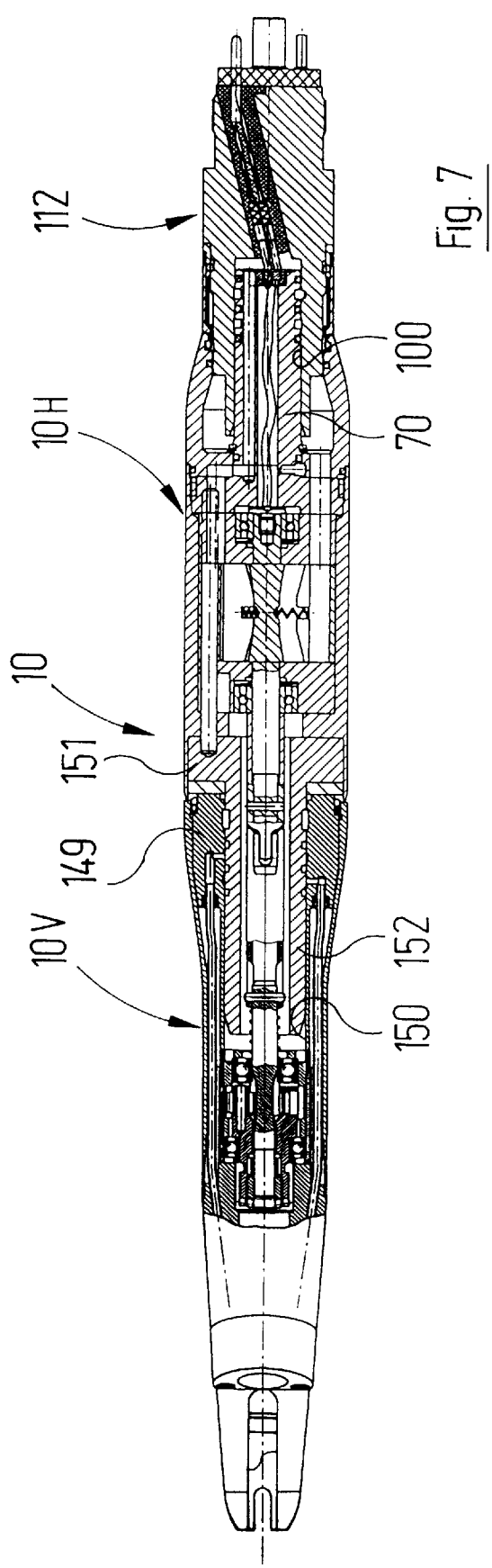

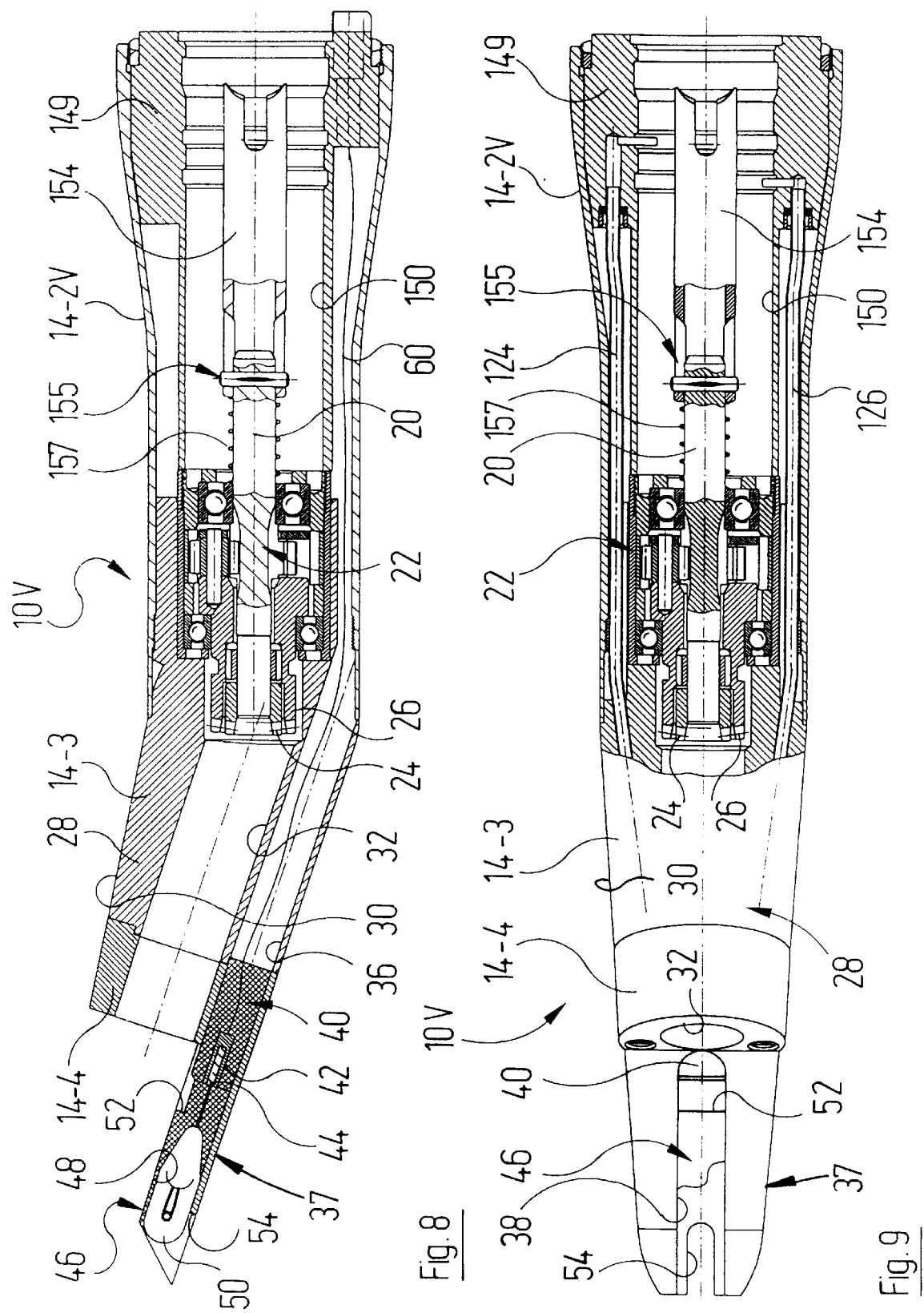

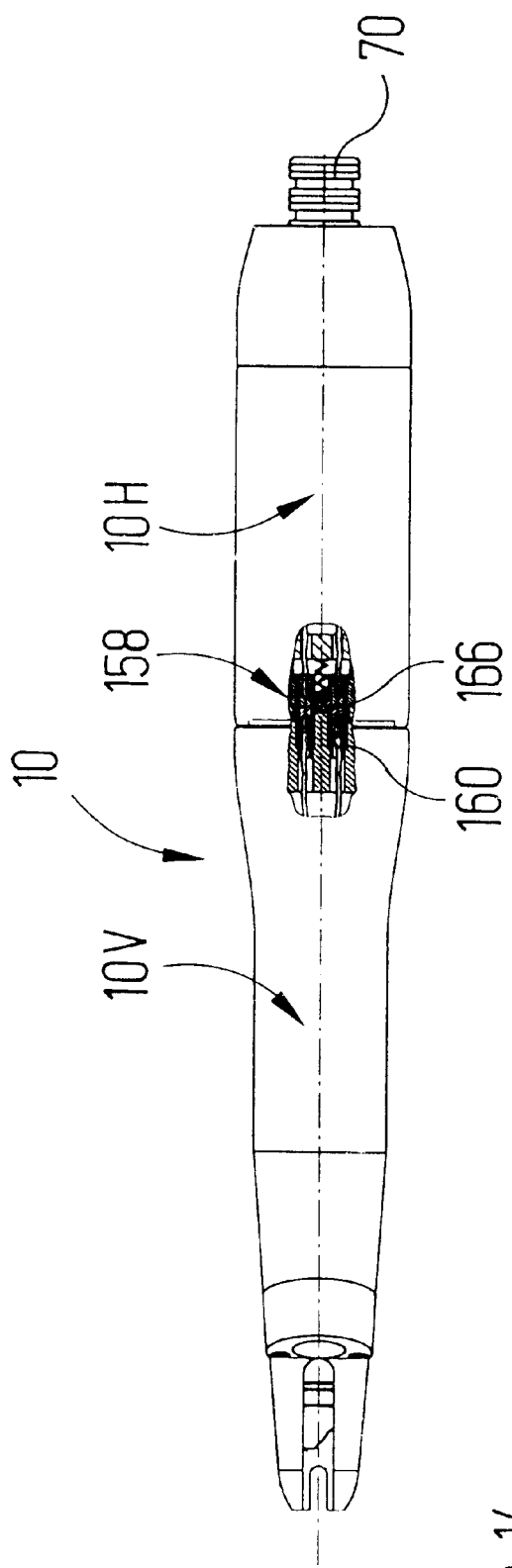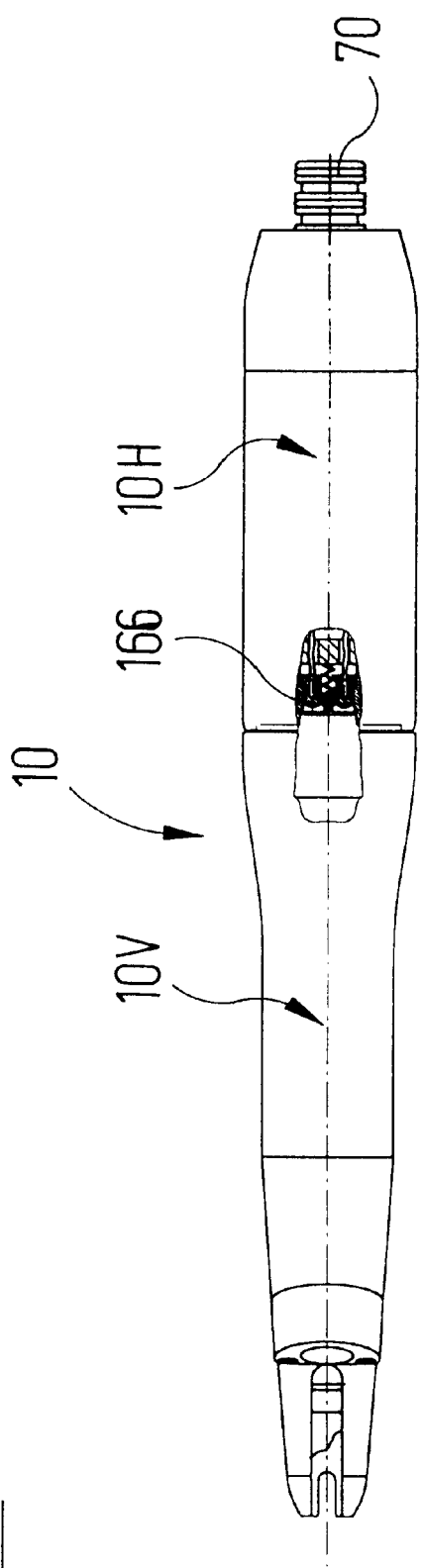

DENTAL HANDPIECE

FIELD OF THE INVENTION

The invention relates to a dental handpiece with a hand piece housing and with a light source, wherein the light source is arranged on a light source carrier that is detachably connected mechanically and electrically to the handpiece housing.

Handpieces of this type for use at dental operating sites are commercially available.

SUMMARY OF THE INVENTION

The object underlying the invention is to develop further a handpiece of the type mentioned in the introduction in such a way that the light output is improved and the interchange of light sources is simplified.

In accordance with the invention this object is achieved by a dental hand-piece comprising a light-providing front portion, a rear portion connectable to a supply cable, a housing, a light source carrier detachably connected mechanicaliy and electrically to the housing, and a light source arranged on the light source carrier, wherein the light source carrier is formed with a light source receiving receptacle that is open at least in one direction and in which the light source is arranged, and a reflecting surface is arranged at a part of the light source that faces material that does not transmit light so the a corresponding part of the light source is shaded.

In the case of the handpiece according to the invention the light source and a lamp carrier are connected so as to form one unit. This facilitates installation removal, since the halogen bulbs that are used customarily in dental handpieces have only small dimensions and have an outer contour that does not promote gripping. The unit formed by light source and light-source carrier is larger and can be produced with a geometry and a surface condition ensuring easy and secure gripping.

As a result of the fixed spatial relation between the light source and the light-source carrier it is furthermore possible to provide a reflecting surface in those regions in which the outer surface of the light source is covered up by the light-source carrier or housing parts. In the case of the dental handpiece according to the invention a portion of the light generated by the light source consequently exits directly, namely at the location where the light source is not covered up by the light carrier, and the reflecting surface is provided for the remaining region or at least a part of the latter, so that the light generated by the light source is emitted either directly or after reflection.

The reflecting surface may extend over the entire covered region of the outer surface of the light source. This is advantageous with regard to utilisation of the entire amount of light generated by the light source.

The reflecting surface may be a layer of metallic or dielectric material that is deposited by vaporisation onto the outside of the light source. This permits economic production of the reflecting surface with a small thickness of the same. This is advantageous with regard to a mechanical enclosure of the light source by the light-source carrier that is as free from play as possible.

The reflecting surface may either consist itself of material that is resistant to disinfectant or bear a protective layer consisting of material that is resistant to disinfectant, for example a layer of glass that is deposited by vaporisation.

Such a handpiece can be treated with commercial disinfecting materials with a view to hygienically unobjectionable re-use.

The reflecting surface may be resistant itself to conditions for sterilisation by superheated steam or bear a protective layer that is resistant to these conditions, for example a layer of glass that is deposited by vaporisation. Such a handpiece can also be sterilised by means of superheated steam.

The light source carrier may be received in positive manner in an associated receptacle of the handpiece housing. This is chosen with regard to clean acceptance of conventional, axially symmetrical light sources.

The receptacle for the light source carrier pertaining to the handpiece housing may be cylindrical or partly cylindrical, one wall of the receptacle for the light source carrier preferably having an angular extent of 190° C.–300° C., preferably of about 210° C.–270° C. so that its two free axial longitudinal edges form an engagement slot. This is advantageous with regard to simple gripping of the light-source carrier for the purpose of removal of the same.

The cylindrical or partly cylindrical light source carrier may comprise an engagement means in a section adjacent to the engagement slot. This facilitates removal of the tight-source carrier together with the light source carried by it.

The engagement means adjacent to the engagement slot may be an engagement groove that passes Through to the rear front face of the light source carrier. This enables the light-source carrier to be constructed overall as a part that is free of any undercut and that can be produced in a simple bipartite injection mould.

The light source carrier may comprise contact parts that cooperate in elastic frictional engagement with mating contact parts that are borne by the handpiece housing. If so, one and the same parts perform both the function of establishing electrical connections between light-source carrier and base part of the handpiece and at the same time the function of mechanical securing of the light-source carrier to the base part of the handpiece. Consequently the fit between the outer surface of the light source and the inner surface of the light-source receptacle can be chosen to be somewhat larger, and in this way fluctuations in the geometry of the surfaces located opposite one another that are conditioned by manufacture can be taken into account.

The handpiece housing may comprise a base part housing and an operating part housing that is detachably borne by said base part housing and wherein the receptacle for the light source carrier is formed at the end of a projecting shoe section of the base-part housing which overlaps the operating-part housing in the axial direction by a distance that is chosen so as to ensure that the light emerging from the light-source carrier fully illuminates the environment of the operating end of a tool that is supported in an operating part of the handpiece to which the operating-part housing pertains. This ensures that depending on the operating part that is mounted onto the base part, the handpiece can be used for various operations in which, equally, an emission of light is achieved that fully illuminates the operating site of the workpiece.

The operating part of the handpiece may comprise a sleeve section embracing the shoe section of the base part housing. With this development an inevitable alignment of the operating part with the light source is obtained, whereby the positive-closure connection formed by the shoe section of the base part of the handpiece and the sleeve section of the operating part can also serve at the same time as a mechanical connection and torque support for the operating part.

The drive motor may be arranged in the handpiece housing wherein the handpiece housing comprises a line channel which is located radially outside the drive motor and in which supply lines leading to the light source are installed. This enables a supply of current to the light source though the interior of the handpiece. Such a handpiece can be connected with variable angular orientation to an energy coupling piece that is borne by the end of the supply cable.

The handpiece may comprise a cylindrical supply connection piece that comprises contact means for the current supply of the light source, wherein the contact means are arranged coaxially with respect to the axis of the supply connection place, being preferably at the same time coplanar in the free front face of the supply connection piece. This development is advantageous with regard to establishing the current connection by using resilient contact elements, in which regard the diverse electrical contacts do not impair the separation of the handpiece from the supply-coupling part. Such a handpiece may further comprise an adapter part that comprises a cylindrical coupling bore, into which the connection piece is capable of being introduced and comprises mating-contact elements that are prestressed in resilient manner with respect to contact means. The resilient, axially effective mating-contact elements are advantageous with regard to good electrical contact and do not impede a close fit of the supply-coupling part and the supply connection piece.

Since, as a rule, a handpiece also contains several energy-consumers- for example, an electric or fluid-operated drive motor for a tool—the handpiece has to comprise a plurality of connectors. Mechanically it is particularly easy to construct these connectors as sleeve-shaped or rod-shaped connector elements. These must then have different radial positions. The adaptor part may comprise a mating contact carrier that extends in a direction that is inclined in relation to the longitudinal axis of the adapter and which at its free end comprises connecting pins that are radially spaced from the longitudinal axis of the adapter. With this further development the connection of coaxial contact elements of the handpiece to eccentric connector elements is established in simple and precise manner.

The mating contact carrier may have the form of a cylindrical rod and is arranged, preferably in detachable manner, in a contact-carrier bore in the adapter part that is inclined in relation to the longitudinal axis of the adapter. This development is advantageous with regard to simple geometry of the mating-contact carrier and of the receptacle that is provided for it in the housing of the adapter part.

The receptacle for the light source carrier may be provided in a rear region of the handpiece housing and wherein a light guide extends from the receptacle for the light-source carrier to the front end of the handpiece housing. This permits simple removal and installation of the light-source carrier and ensures utilisation of the entire amount of light emitted by the light source. The light source itself, however, is remote from the operating end of the handpiece, this being preferred for many Applications (for example, on account of the heat generated by the light. source).

In this regard the production of the receptacle for the light-source carrier and the installation and removal of the light carrier are particularly simple if the receptacle for the light-source carrier is an axial bore that emanates from the rear front face of the handpiece housing.

For many applications it is advantageous if the base part of the handpiece consists of two detachably connected base-part segments - for example, if it is desired to make available handpieces with different degrees of bending or handpieces with different drive motors or handpieces with different gear transmissions. In this case the supply of current to the light source is then preferably effected by the two detachable base-part segments being located axially in sequence, the two segments comprising electrical connecting parts whereby preferably one of these connecting parts is prestressed by spring tension with respect to the other connecting part.

The connecting part borne by the rear base-part segment may bear an axially projecting spacing means and the connecting part of the front base part segment may comprise a recess with which the spacing means can engage. This ensures that the contacts provided in the front face of the rear base-part segment are protected by a spacing means against approach of a metallic part, which would result in a short-circuit between the mating-contact elements. A front base-part segment containing a light-source carrier can establish a connection to the mating-contact elements by reason of a complementary recess provided in it, into which the spacing means is capable of being introduced. Other front base-part segments which do not include a light-source carrier and accordingly are not provided with a corresponding complementary recess may, on the other hand, be mounted onto the rear base-part segment without any risk of a short-circuit.

The handpiece may be a straight handpiece having a plurality of axial receptacles for light-source carriers which emanate from its free front face which are preferably evenly distributed in the peripheral direction and each receive a light-source carrier with associated light source. With this further development it is possible to emit operating light in different directions. This is advantageous, in particular, in conjunction with tools that can be disposed with variable orientation on the rectilinear handpiece. Such a handpiece may further comprise supply lines separated by the light source carriers which are guided to connecting pins located at the rear end of the handpiece housing. This permits the light sources that are provided at the free end of the handpiece to be variably connected. Such a hand piece may further comprise means for mutually independent adjustment of the currents that flow through the various light sources, whereby the magnitude of the various supply currents is preferably continuously adjustable. This enables the amounts of light emitted by the various light sources to be variably adjusted, preferably continuously.

BRIEF DESCRIPTION

Examples of embodiments of the invention are elucidated in more detail below with reference to the drawings.

For the sake of better clarity of layout, details pertaining to the various embodiment examples are in each case provided with reference symbols only in a subset of the figures relating to the particular embodiment example. These details can be easily recognised and identified in those figures which are not provided with reference symbols. Corresponding text passages apply equally to them. This also applies with respect to modified embodiment examples.

Where necessary for the purpose of differentiation, different embodiment examples are distinguished by suffixes to the reference symbols "-A", "-B" etc. If suffixes are not present, the remarks apply equally to all embodiment examples.

The expression "front" is used in the sense of "adjacent to the tool or to the free end of the handpiece oil pointing in that direction", the expression "rear" is used in the sense of "adjacent to the supply end of the handpiece or pointing in that direction".

Also, particulars of an embodiment example relating functionally to particulars of an embodiment example that has already be previously are not described again in any detail.

Figure 2:
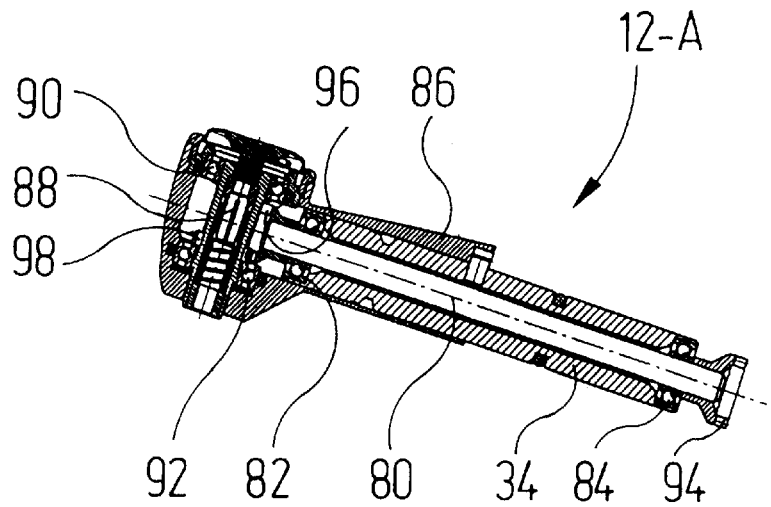
Figure 3:
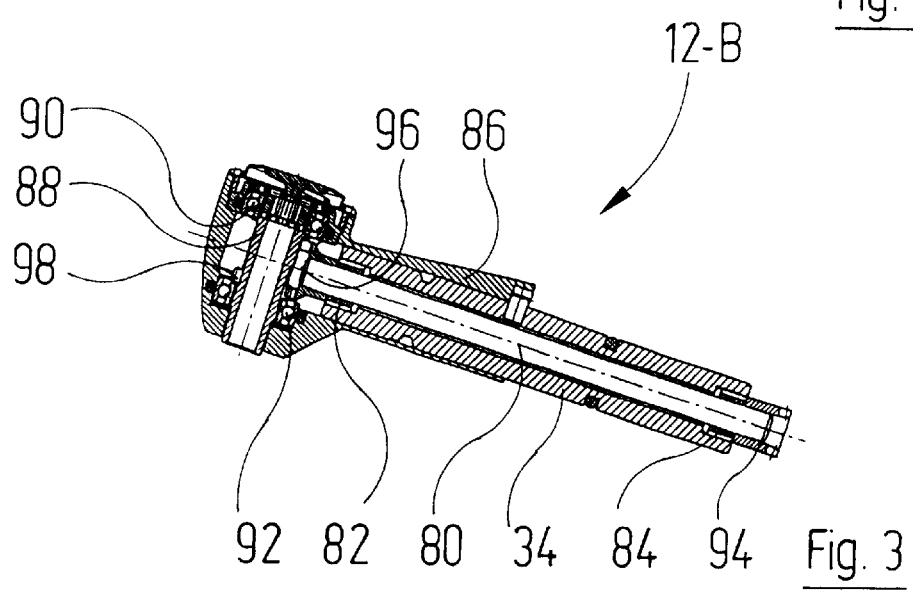
Figure 4:
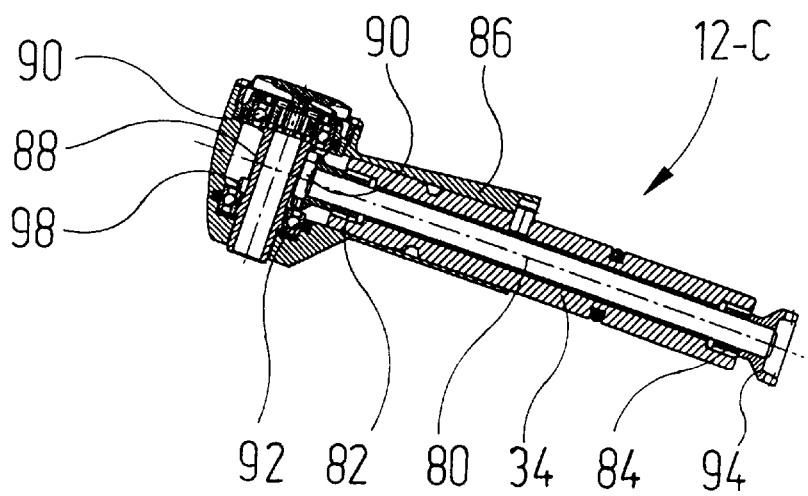
Figure 5:
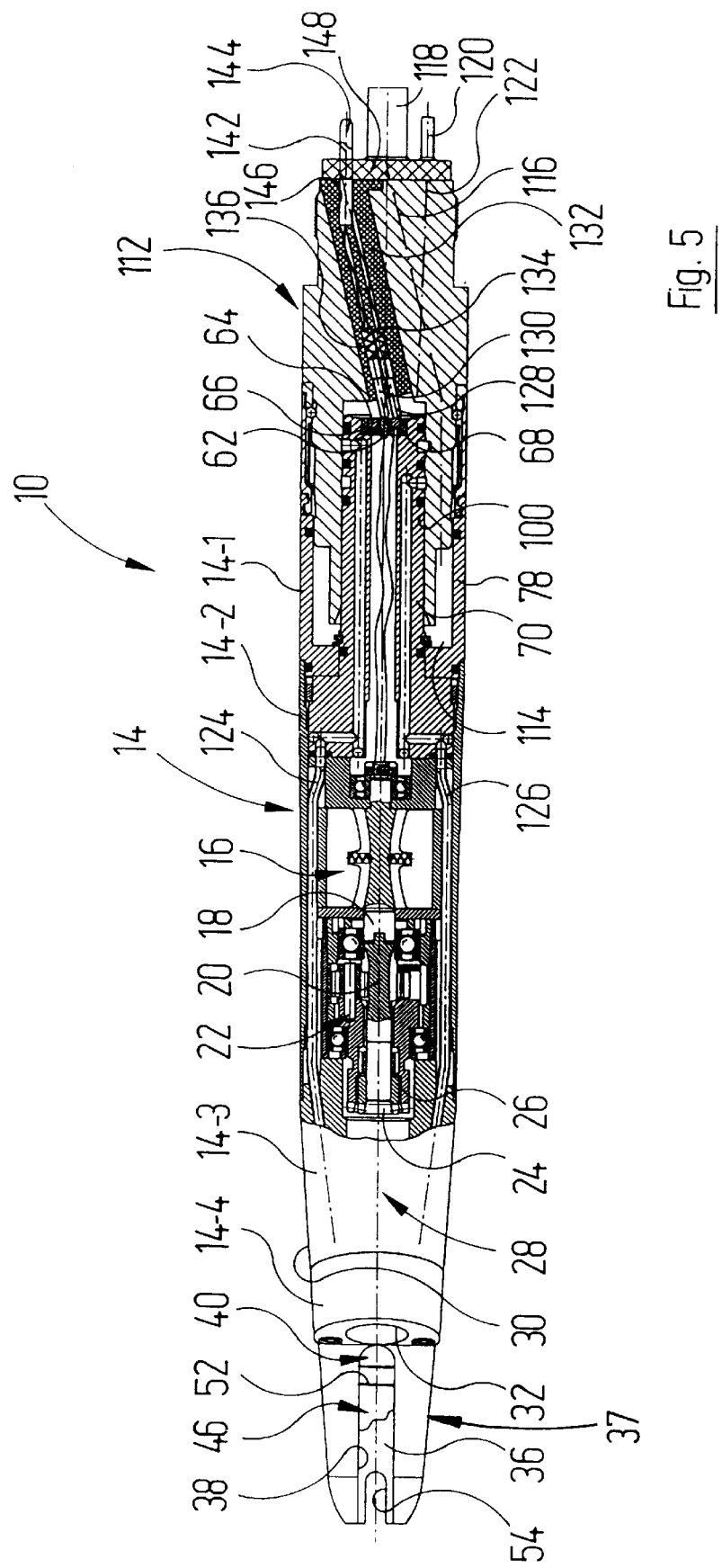
Figures 10, 11:
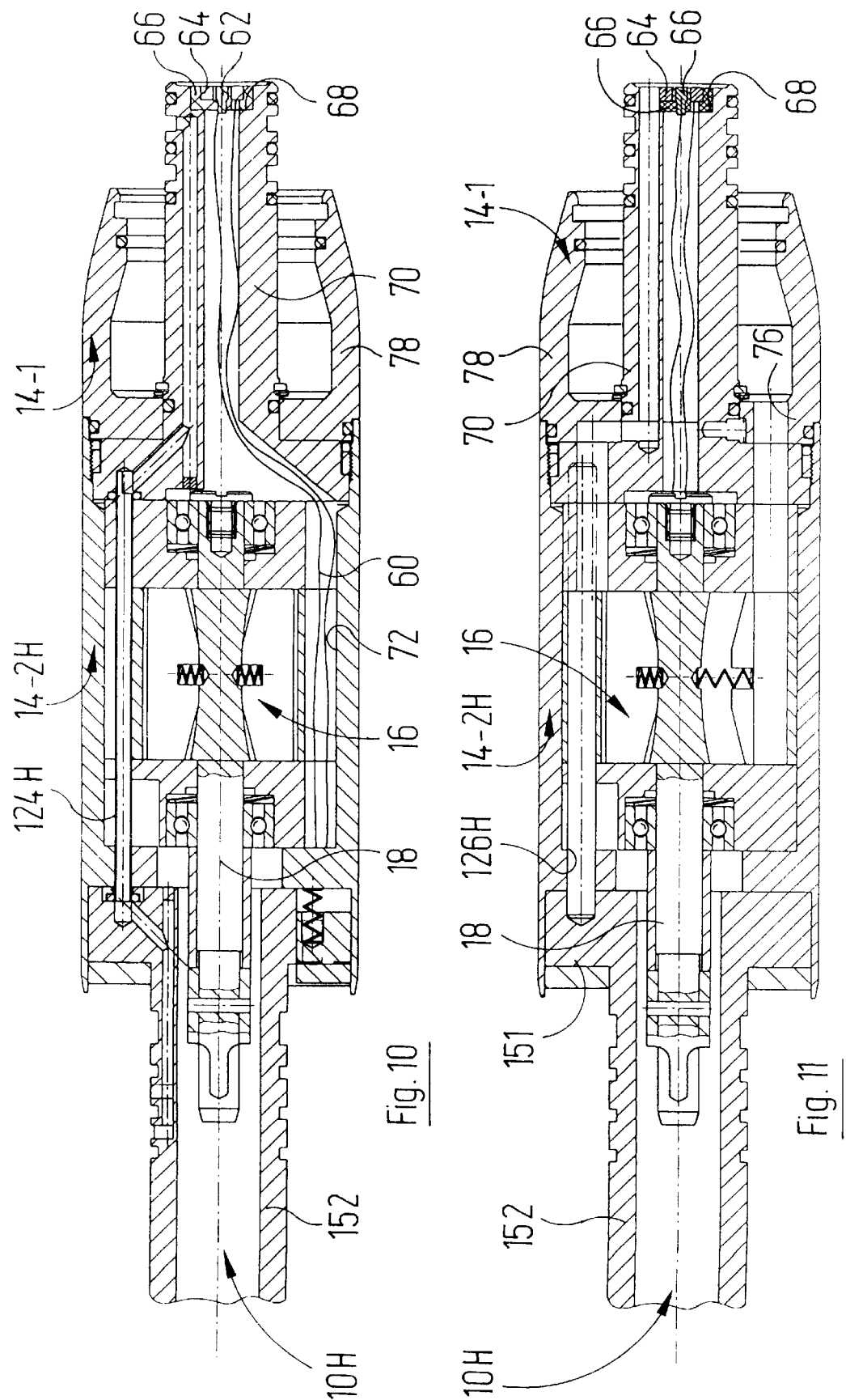
Figure 12:
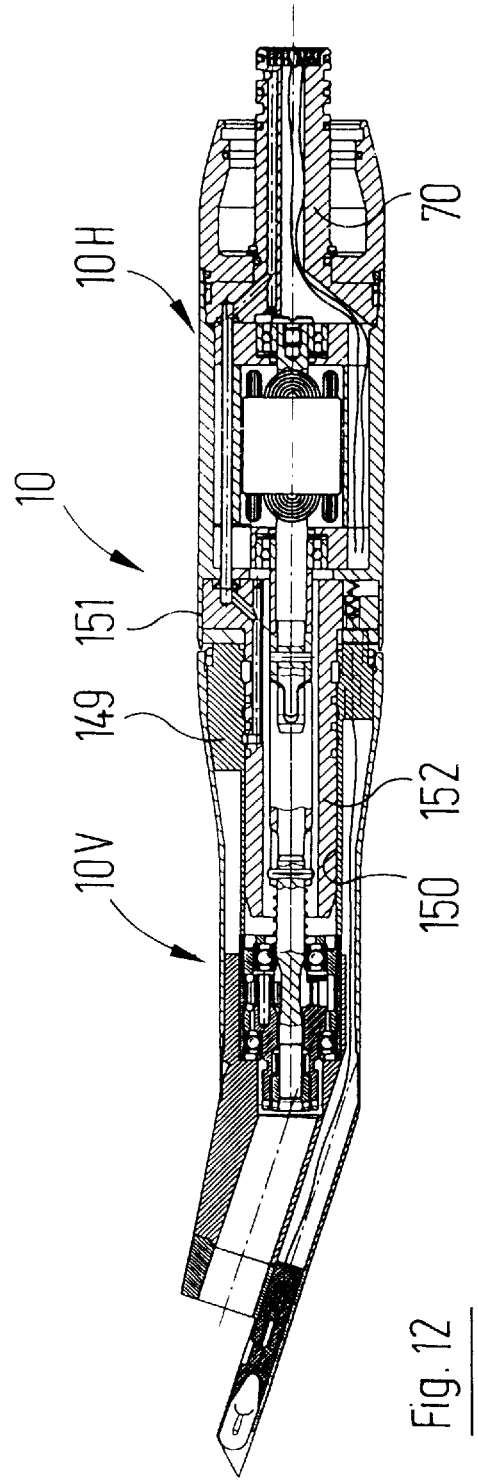
Figure 13:
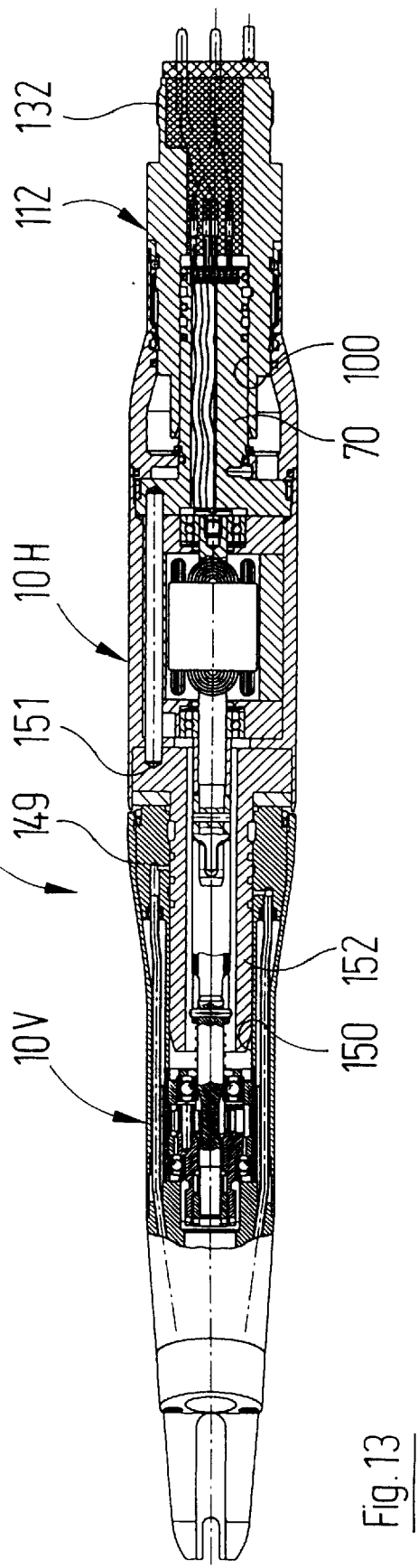
Figure 16:
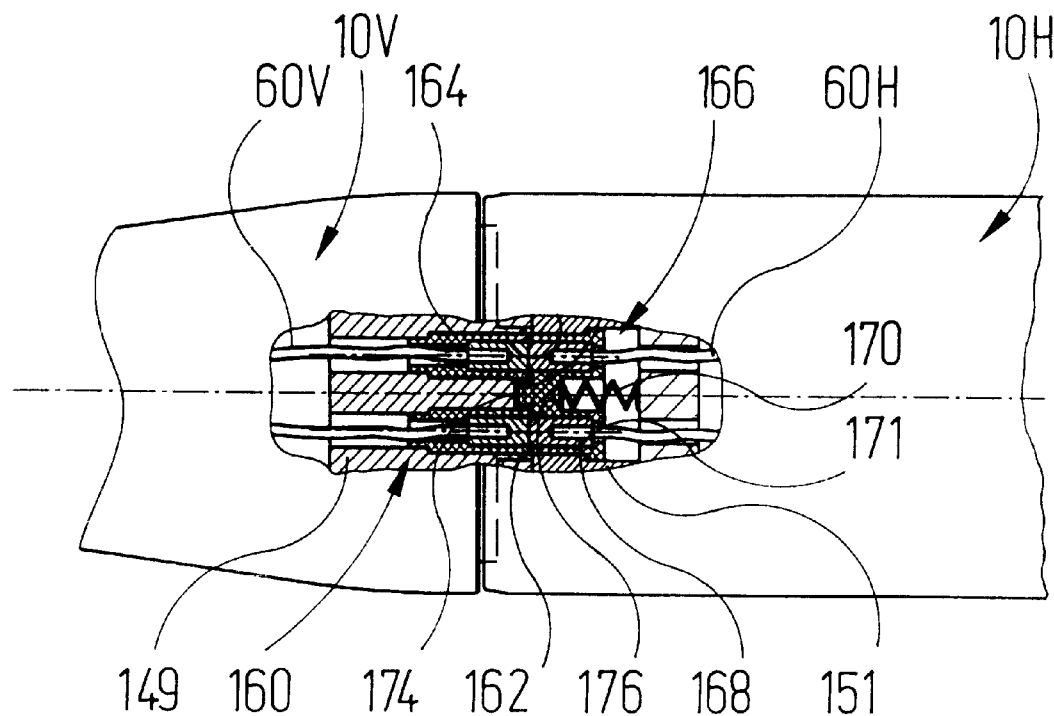
Figure 17:
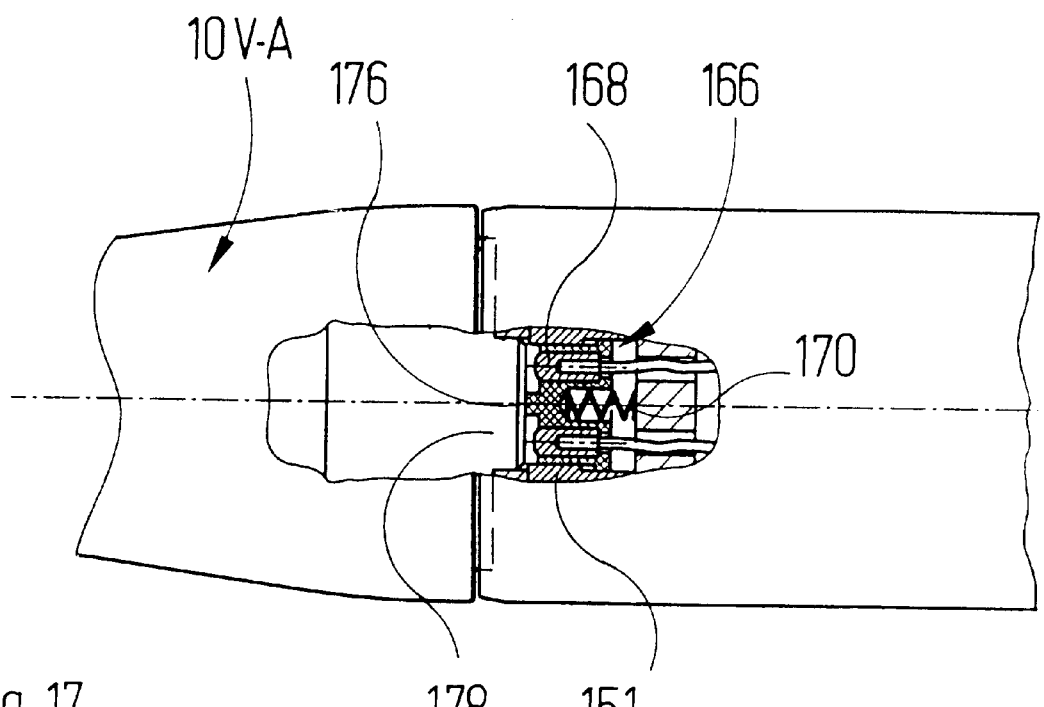
Figure 18:
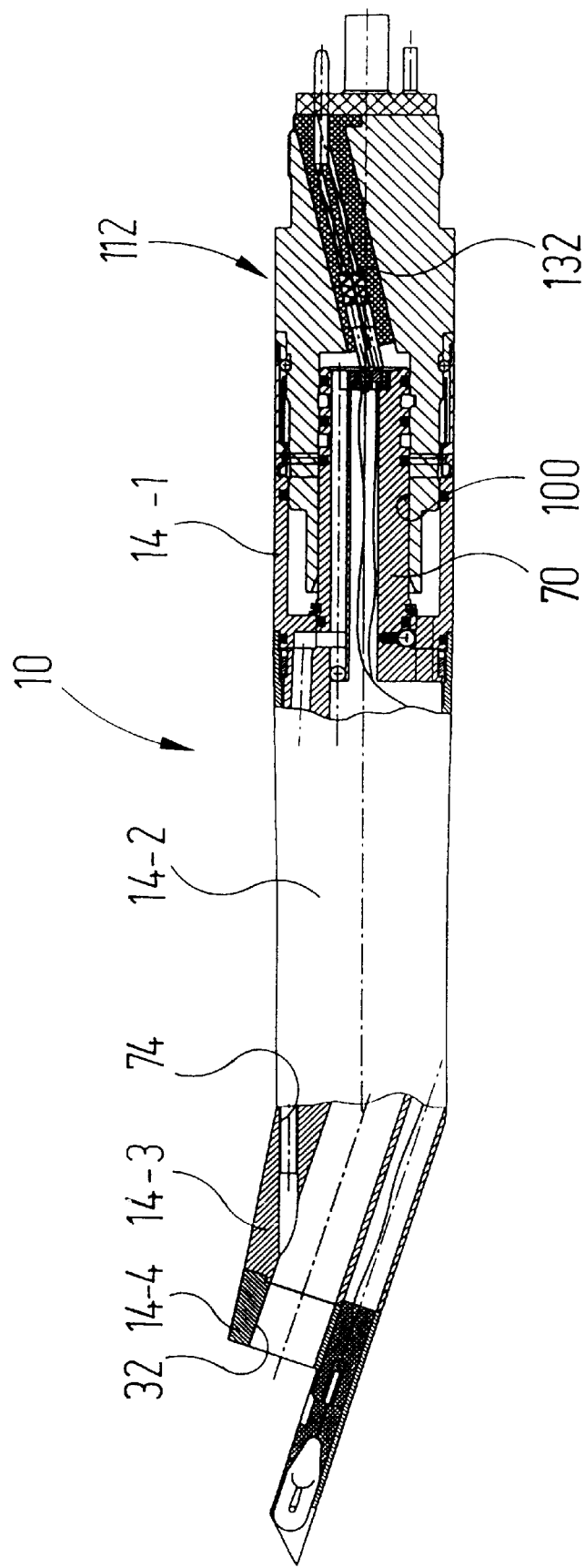
Figures 19, 20, 21:
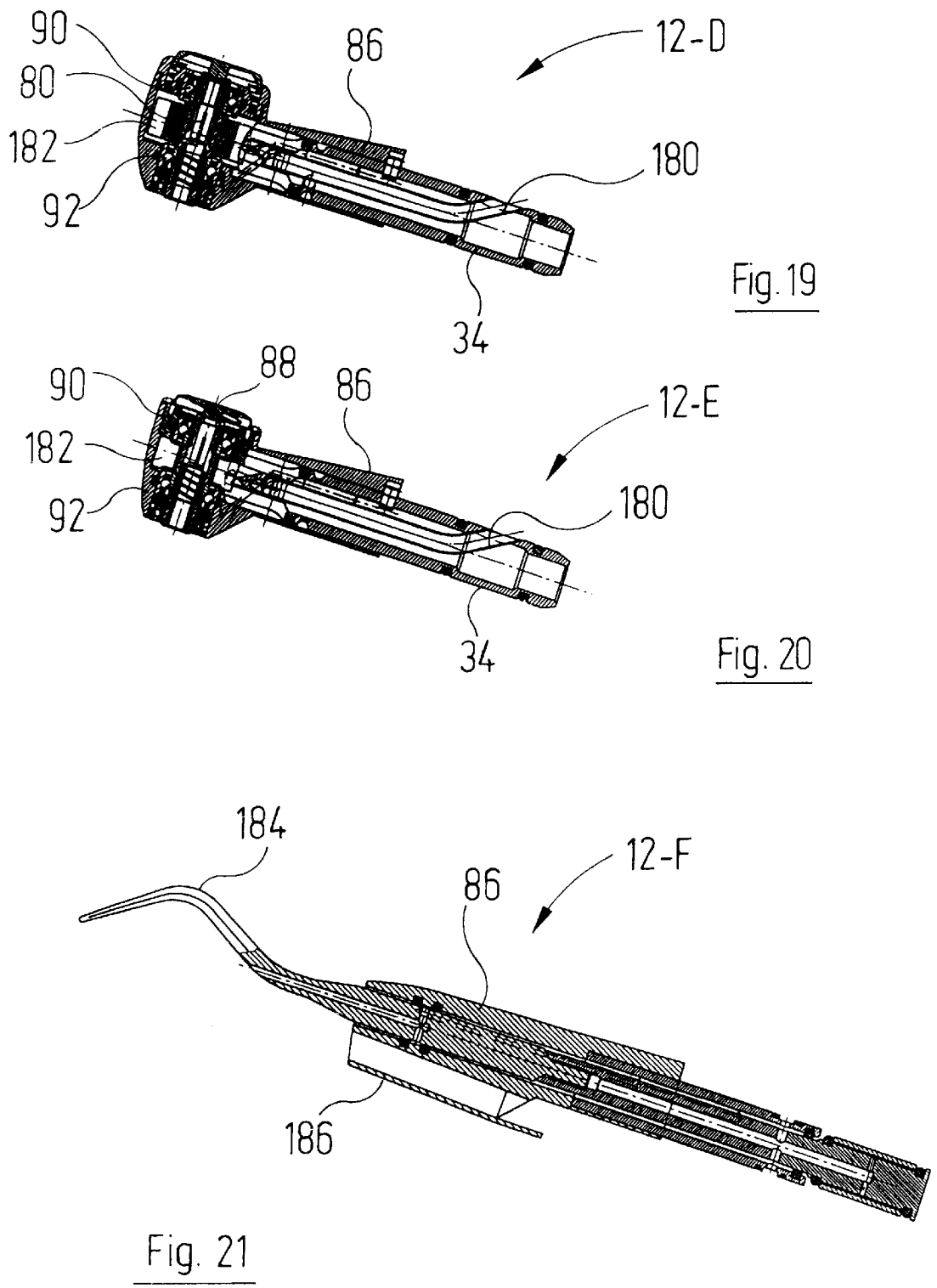
Figure 22:
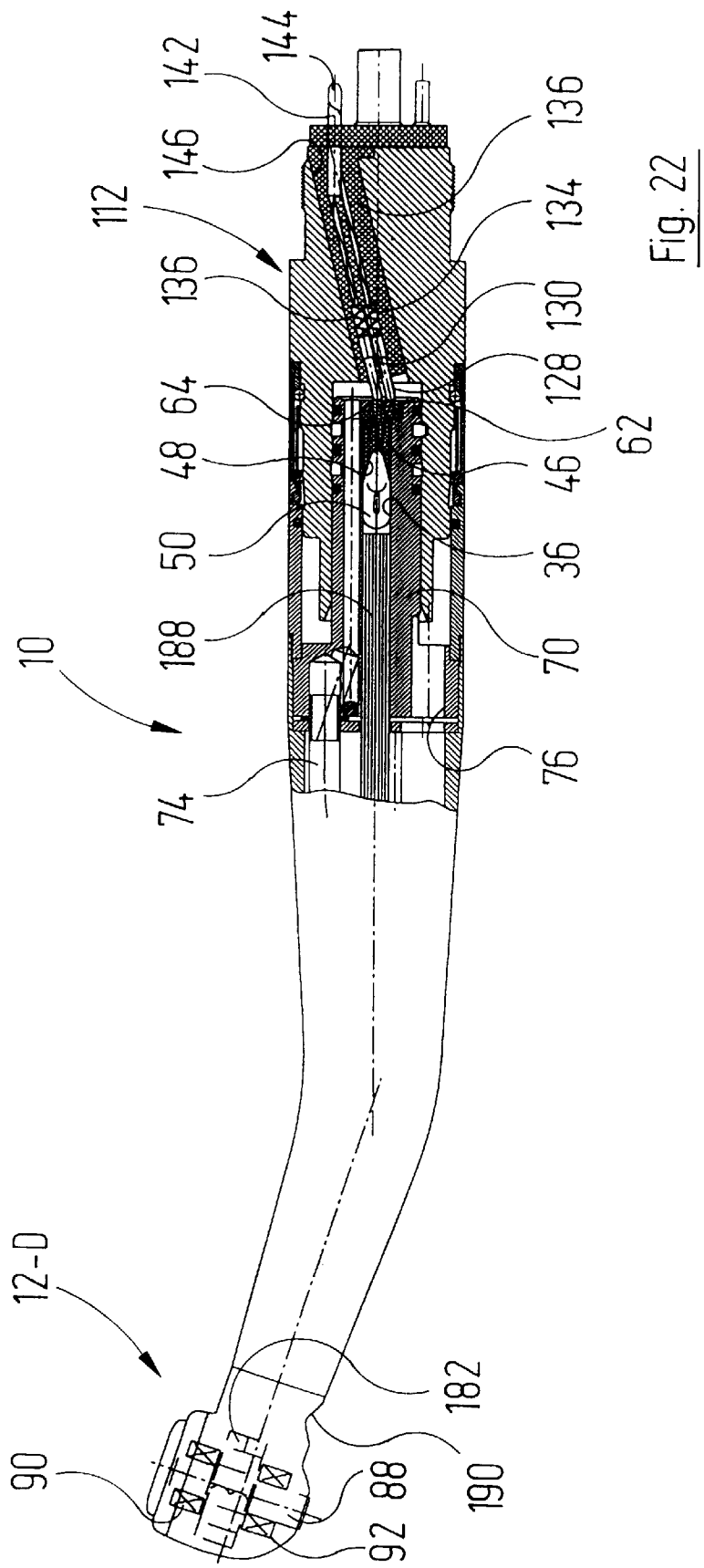
Figure 23:
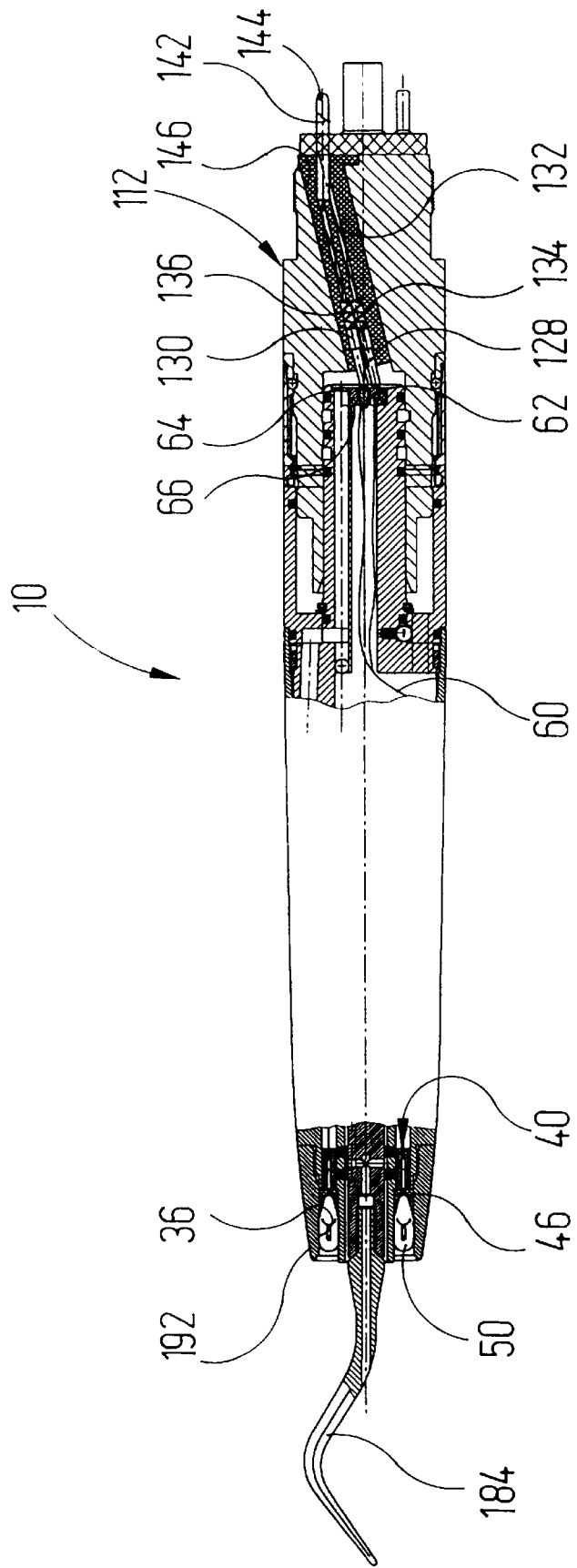
Figure 24:
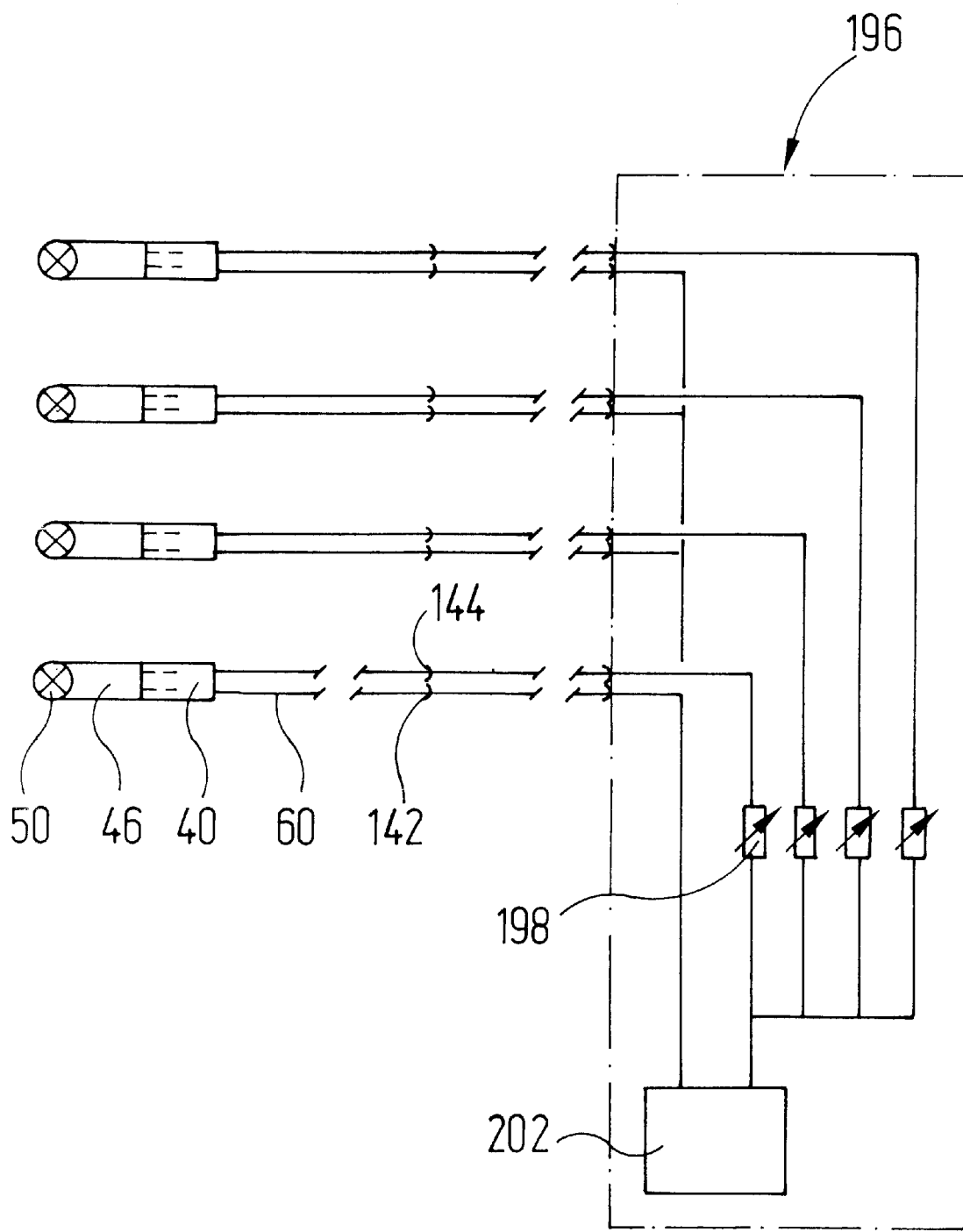
Figure 25:
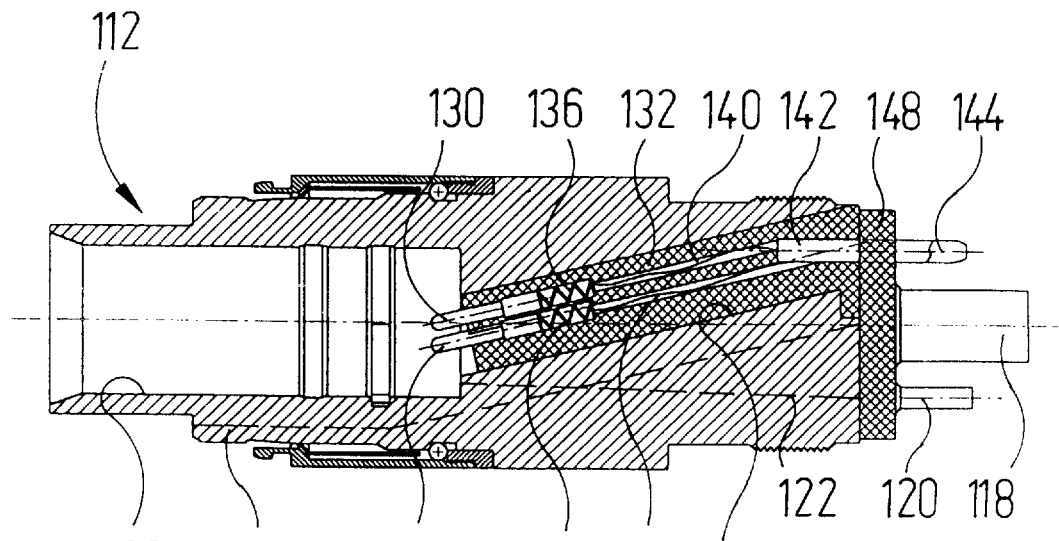
Figure 26:
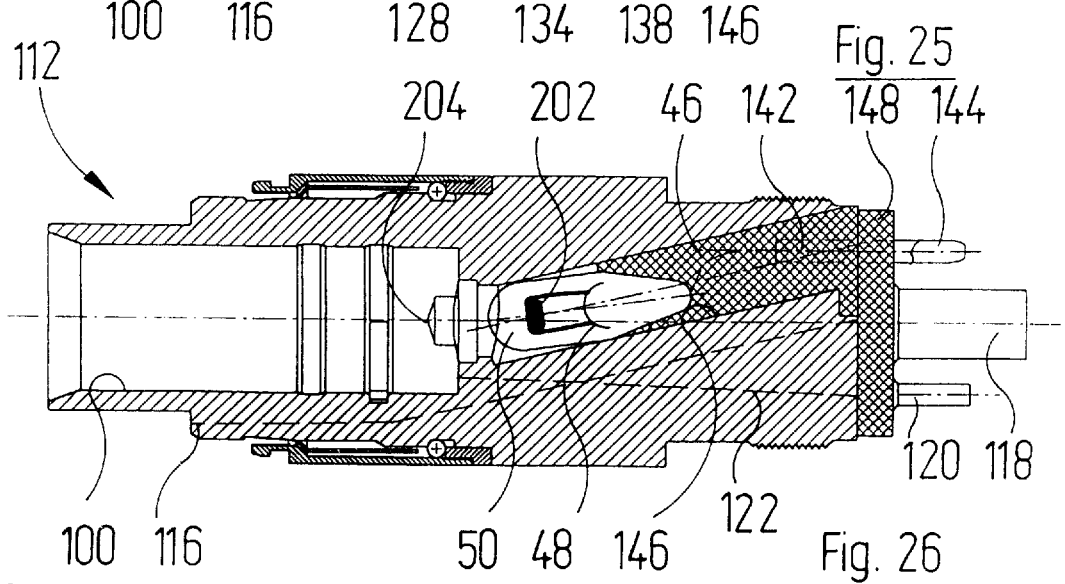
Figure 27:
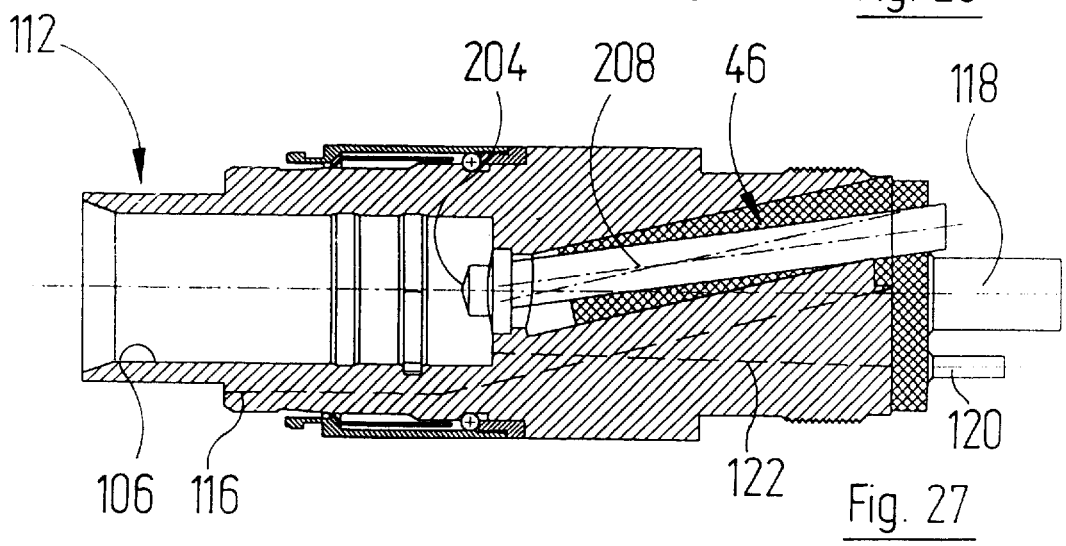

In the drawing there are shown in detail:

FIG. 1: a longitudinal section in the axial plane of symmetry of the base part through a base part of a dental handpiece;

FIGS. 2–4: axial sections through various operating heads that can be detachably mounted onto the base part of the handpiece shown in FIG. 1 for different operations;

FIG. 5: a top view of the base part of the handpiece shown in FIG. 1, partly cut away in an intersecting plane perpendicular to the longitudinal median plane;

FIGS. 6,7: sectional news which correspond to FIGS. 1 and 5 but which show a different embodiment example including two detachably connected segments;

FIGS. 8,9: sectional views corresponding to FIGS. 6 and 7, in which a front segment of the handpiece is reproduced on an enlarged scale;

FIGS. 10,11: views similar to FIGS. 6 and 7, in which the rear segments of the handpiece are reproduced on an enlarged scale;

FIGS. 12,13: sections similar to FIGS. 6 and 7 through a modified handpiece with electric drive;

FIG. 14: a top view of a handpiece according to FIGS. 6 and 7 or according to FIGS. 12 and 13, partly cut away in an axially parallel plane, in which details of an electrical connection between the two handpiece segments are represented;

FIG. 15: a view similar to FIG. 14, whereby, however, the front handpiece segment includes no electrical consumers;

FIGS. 16,17: enlarged representations of the regions of the handpiece shown cut away in FIGS. 14 and 15;

FIG. 18: a section corresponding to FIG. 1 through a further modified handpiece;

FIGS. 19–21: axial sections produced in the longitudinal median plane through tools that can be used together with the handpiece in FIG. 18;

FIGS. 22,23: lateral views, partly cut-away axially, of other modified handpieces;

FIGS. 24: a schematic circuit diagram of the voltage supply for a handpiece bearing several incandescent lamps, and FIGS. 25–27: axial sections through adapter parts that can be used together with handpiece shown in the preceding figures or, on the other hand, with further modified handpieces.

Designated overall by 10 in FIG. 1 is a base part of a handpiece, onto which different handpiece operating parts can be detachably mounted—for instance, one of the handpiece operating parts 12-A, 12-B, 12-C shown in FIGS. 2–4. Together with an operating part 12 the base part 10 forms a dental handpiece.

As is evident from FIG. 1, the base part 10 has a base-part housing 14 composed of several segments 14-1, 14-2, 14-3, 14-4 located axially in sequence.

Inside the base-part housing 14 various mechanical drive parts are accommodated. A rotating-piston air engine 16 has a drive shaft 18 which is connected via a plug-in, positive-closure connection to the input shaft 20 of a planetary gearing 22.

On the free end of the input shaft 20 that passes through the planetary gearing 22 a cup-shaped pinion 24 is seated which consequently revolves at the rotary speed of the rotating-piston air engine 16.

Connected to the planet carrier of the planetary gearing 22 is a second cup-shaped pinion 26 which revolves at reduced rotary speed corresponding to the reduction ratio of the planetary gearing 22.

An angled housing section 28 of the base-part housing which extends over the housing segments 14-3 and 14-4 has an outer surface 30 tapering conically and a central bore 32, into which a cylindrical shaft housing 34 of an operating part 12 (cf. FIGS. 2–4) is capable of being introduced in close fit.

Located below the housing section 28 is a cylindrical lamp-carrier receptacle 36 pertaining to the base-part housing 14. Said receptacle is guided out in a shoe section 37 projecting in the longitudinal direction of the base part 14 above the front face of the housing section 28, whereby it comprises in the protruding section an engagement slot 38 that is open in the upward direction. The peripheral extent of the engagement slot 38 amounts to between approximately 60° and 170° (preferably between 90° and 150°); correspondingly the peripheral extent of the remaining wall of the lamp-carrier receptacle 36 is between 300° and 190° (preferably between 270° and 210°).

A cylindrical connector part 40 which is made of insulating plastic material is inserted into the lamp-carrier receptacle 36 subject to frictional engagement. Cast into the connector part 40 are two spaced axial female contacts 42. The latter cooperate in elastic frictional engagement with contact pins 44 that protrude in the axial direction beyond the rear front face of a lamp carrier 46. In this manner the lamp carrier 46 and the incandescent lamp 50 carried by it are at the same time mechanically and electrically connected to the base part 10.

The lamp carrier 46 has a substantially cylindrical outer contour and is pushed into the end of the channel 36 subject to close clearance.

The lamp carrier 46 has a lamp receptacle 48 in which an incandescent lamp 50, preferably a halogen lamp, is received in positive manner. The lamp carrier 46 is preferably moulded onto the incandescent lamp 50.

Integrally moulded at the rear upper end of the lamp carrier 46 is an engagement groove 52 which is open in the direction towards the rear front face of the lamp carrier 46, so that the lamp carrier 46 is a plastic part that can be produced in undercut-free manner in a bipartite injection mould.

In the foremost region of the lamp-carrier receptacle 36 the lowest section of the wall of the lamp-carrier receptacle is removed, so that an additional lower light-exit window 54 is obtained which is supplementary to the open end of the lamp-carrier receptacle 36.

As is evident from the cut-out representation of FIG. 1, a reflecting layer 56 is located between the outer surface of the incandescent lamp 50 and the inner surface of the lamp receptacle 48. Said reflecting layer extends over the entire overlapping region pertaining to incandescent lamp 50 and lamp receptacle 48.

If the lamp carrier 46 is moulded onto the incandescent lamp 50, as stated above, then prior to extrusion-coating of the incandescent lamp the reflecting layer 56 is generated on the surface region of the incandescent lamp that is later covered up. This can be effected, for example, by vapour-coating of the lamp with aluminum or another suitable reflecting material. In the course of the vapour-deposition process the part of the lamp surface that later is not surrounded by the material of the lamp carrier 46 and not covered up by housing parts remains exposed, for which reason these surface parts may be covered up in the course of vapour-coating with a suitably shaped mask part, into which the front lamp end is inserted in the course of vapour-coating.

If use is made of a lamp carrier 46 into which an incandescent lamp 50 can be detachably inserted (by using a connecting thread, for example), then the reflecting layer 56 is preferably generated on the lamp carrier 46 and optionally on the housing parts covering up the incandescent lamp. This is then effected by vapour-coating or galvanic application of a reflecting layer.

It should be understood that, instead of metallic reflecting layers, use may also be made of dielectric reflecting layers.

The reflecting layer 56 may, in addition, bear on its outside a protective layer 58 that is resistant to disinfectants used in dental surgeries and that withstands the operating conditions utilised in connection with sterilisation by superheated steam. Such a protective layer may, for example, be constituted by glass that is deposited by vaporisation.

If the lamp carrier 46 is moulded onto an incandescent lamp 50, the protective layer 58 can be dispensed with.

From the connector part 40 there extend two electrical supply lines 60, one end of each of which is connected to the female contacts 42 and the other end of each of which is connected respectively to a central cylindrical contact 62 arid an annular contact 64 that is coaxial and coplanar with said central cylindrical contact. These two contacts are provided on an insulating piece 66 which is inserted in a recess 68 sunk in the free front face of a supply connection piece 70 pertaining to the base-part housing 14 that is located on the right in FIG. 1. The supply connection piece 70 has a central line channel 72, through which the supply lines 60 extend, and a compressed-air channel 74, via which the rotating-piston air engine 16 is supplied with compressed air. An exit-air channel 76 opens into an annular space located between a peripheral wall 78 of the housing segment 14-1 and the supply connection piece 70.

The operating parts of the handpiece shown in FIGS. 2–4 each have a drive shaft 80 that extends through the shaft housing 34 and is supported in the latter via bearings 82, 84.

In operating-part housings 86 pertaining to the handpieces 12, clamping sleeves 88 for drill shanks are rotatably supported by means of bearings 90, 92. In the case of the embodiment example according to FIG. 2 the clamping sleeve 88 takes the form of a slotted sleeve.

On the drive side the drive shafts 80 bear a pinion 94, whereby in the case of the operating parts according to FIGS. 2 and 4 the pinions 94 have such a radial dimension that they cooperate with the pinion 26 of the base part 10 that runs more slowly, whereas in the case of the embodiment example according to FIG. 3 the pinion 94 matches the pinion 24 of the base part 10.

On the driving part the drive shafts 80 bear pinions 96 that are toothed on the front face and cooperate with a toothed wheel rim 98 which is connected in non-rotating manner to the clamping sleeve 88.

The axial dimension of the part of the shaft housing 34 protruding beyond the operating-part housing 86 is so chosen that the rear front face of the operating-part housing 86 abuts the front face of the housing section 28 if correct engagement conditions obtain between the pinion 24 (or 26) and the pinion 94 of the operating part 12.

As is evident from FIG. 5, the supply connection piece 70 fits into a blind bore 100 of an adapter part 112 that is shown in FIG. 24 (sic) on an enlarged scale. Said adapter part engages, in turn, the end section 78 of the housing so as to be capable of meshing. From the annular space 114 delimited between the adapter part 112 and the peripheral wall 78 an exit-air channel 116 extends to an exit-air connection piece 118.

A compressed-air connection piece 120 pertaining to the adapter part communicates with an annular groove in the end of the supply connection piece 70 via a compressed-air channel 122 in order to supply compressed air to the pressure side of the rotating-piston air engine 16 via the compressed-air channel 74.

Further connecting connection pieces are provided, in order to supply fluid to spray-water and spray-air channels 124, 126 via intermediate channels in the base part of the handpiece which are not shown in any detail.

Contact bodies 128, 130 that are capable of being displaced in a contact carrier 132 contrary to the force of springs 134, 136 cooperate with the central contact 62 and the contact 64 that is coplanar and coaxial with it in the front face of the supply connection piece 70. Connecting leads 138, 140 extend through the contact carrier 132 to connecting pins 142, 144.

The contact carrier 132 has a cylindrical outer surface and is received in a contact-carrier bore 146 that extends, proceeding from the axis of the adapter part 12, obliquely outwards to the rear end of the adapter part 112.

A flat gasket 148 is shown at the free end of the adapter part 112.

The adapter part 112 is connected in turn to a coupling part which is not represented in the drawing and which is disposed at the end of a supply cable that contains current-supply lines and also fluid-supply and fluid-disposal lines.

The embodiment example according to FIGS. 6–11 differs from the example previously described principally in that the base part 10 is subdivided into a front segment 10V and a rear segment 10H.

Hence it is possible, in conjunction with a single rear base-part segment 10H containing the rotating-piston air engine 16, to make use of several different front base-part segments 10V. These may differ, for example, in the transmission ratio of the planetary gearing 22 and/or in the setting angle of the bore 32 in relation to the longitudinal axis of the base part 10 (including setting angle 0ø, so that a straight handpiece is obtained).

To this end a front base-part housing segment 14V with an end piece 149 is provided with a coupling bore 150, with which a coupling connection piece 152 engages in close fit that protrudes from the rear base-part housing segment 14H to the left in the drawing and is borne by an end part 151 of said base-part housing segment. The base-part housing segment contains an intermediate shaft 154, via which the drive shaft 18 of the rotating-piston air engine 16 is connected to the input shaft 20 of the planetary gearing 22.

The connection of the intermediate shaft 154 to the input shaft 20 is effected via a pin/elongated-hole connection 155 which is prestressed into the extended position by means of a spring 157.

The two base-part segments 10V and 10H are, moreover, interconnected with the aid of a detachable locking mechanism which is not reproduced in any detail in the drawing.

The embodiment example according to FIGS. 12 and 13 largely corresponds mechanically to that according to FIGS. 6–11 but includes an electric micromotor 156 instead of a rotating-piston air engine 16. Correspondingly, the front face of the supply connection piece 70 now bears an increased number of coaxial and coplanar contacts 124, 126 etc. that cooperate with corresponding contact bodies 128, 130 etc. pertaining to the contact carrier 32. The contact-carrier bore 146 now extends axially, since all the connecting pins 142, 144 etc. relate only to the electrical supply.

As is evident from FIGS. 14 and 15, between the two base-part segments 10V and 10H an electrical connection designated overall by 158 is provided, via which the incandescent lamp 50 is supplied with current. In this regard FIG. 14 shows the case where the rear base-part segment 1OH is used in conjunction with a front base-piece segment 10V that contains an incandescent lamp 50, whereas FIG. 15 shows the case where a front base-part segment 10V-A containing no light source is mounted onto the rear base-part segment 10H.

As is evident from FIG. 16, the connection 158 includes a connecting part 160 arranged at the end of the front base-part segment 10V with a projecting positioning peg 162 and fixed insulated contact parts 164 which are connected to the supply lines 60 leading to the incandescent lamp 50. The front side of the rear base-part segment 1OH bears a complementary insulating connecting part 166 with contact parts 168. The connecting part 166 is capable of being displaced contrary to the force of a helical spring 70 in a complementary recess 171 pertaining to the end part 151.

The connecting part 166 bears a spacing peg 176 which can engage a complementary blind bore 174 that is formed in the front face of the connecting part 160. In this manner the front faces of the contact parts 164 are able to come into contact with the front faces of the contact parts 168.

In the case of a front base-part segment 10V (cf. FIG. 15) that contains no incandescent lamp the end of the base-part segment located on the right in the drawing has a positioning peg 178 that is shorter than the positioning peg 162 of the base-part segment 10V with incandescent lamp (FIG. 14) This positioning peg 178 has no recess in its front face and consequently abuts the front face of the spacing peg 176. Hence the positioning peg 178 cannot short-circuit the contact parts 168.

The base part 10 of the handpiece shown in FIG. 18 contains no drive motor, rather the compressed-air channel 74 passes right into the housing section 28, where it intersects the bore 32.

As is evident from FIGS. 19 and 20, operating parts 12-D and 12-E that can be used with this base part 10 each have a compressed-air channel 180 which leads to a turbine wheel 182 that is connected to the clamping sleeve 88.

The operating parts 12-D and 12-E according to FIGS. 19 and 20 differ by virtue of the dimensions of the turbine wheels.

FIG. 21 shows a scaler operating part 12-F that is likewise capable of being connected to the base part according to FIG. 18. It has a central compressed-air channel 180 which directs compressed air into the vicinity of the free end of a curved scaler tool 184.

The operating-part housing 86 of the operating part 12-E has a sleeve section 186 which fits over the shoe section 37 in positive manner, as a result of which the operating-part housing 86 is secured against rotation.

In the case of the modified embodiment example according to FIG. 22 the lamp carrier 46 Us inserted together with the incandescent lamp 50 into the rear end of the supply connection piece 70, which to this end is provided with a lamp-carrier receptacle 36 emanating from its rear front face. The contacts 62, 64 are arranged directly on the front face of the lamp carrier 46 located on the right in the drawing. The incandescent lamp 50 is metallised on its entire peripheral wall.

The light emitted by the incandescent lamp 50 is passed to a light guide 188 which leads to an exit window 190 provided in the vicinity of the clamping sleeve 88 in such a manner that a pencil of light is obtained which is directed towards the point of a tool that is inserted into the clamping sleeve 88.

FIG. 23 shows a scaler handpiece in which the base part 10 is a straight base part. Incorporated into an end cap 192 pertaining to the base part that is capable of being unscrewed are, distributed in the peripheral direction, several :amp-carrier receptacles 36 formed by bores which each receive an incandescent lamp 50 with associated, integrally moulded lamp carrier 46, as described above, and a contact carrier 40 is provided for each of the lamp carriers.

Equivalent contacts 42 pertaining to the contact carriers 40 are each connected to one of the supply lines 60, so that voltage is applied equally to all the incandescent lamps 50.

In a modification of the embodiment example described above, according to FIG. 24 separable supply lines 60 which each lead to a pair of connecting pins 142, 144 can be provided for each of the contact carriers 66.

In a supply unit 196 for the various incandescent lamps the current intensity of the various incandescent lamps can then be adjusted individually, as indicated schematically in FIG. 24 by adjustable resistors 198, via which the incandescent lamps 50 are connected separately to one pole of a voltage source 200. The other connectors of the incandescent lamps are connected jointly to the second pole of the voltage source 200.

In this manner it is possible to dim or to switch off altogether a portion of the incandescent lamps that is not required or, in the case of special operations, a dazzling portion of the incandescent lamps 50.

In a modification of the embodiment example according to FIG. 22 the lamp carrier 46 can also be constructed in such a way that, according to FIG. 26, it fits into the contact-carrier bore 146 of the adapter part and at the same time performs the function of the contact carrier 132. The axial dimension of the lamp carrier 46 is then such, taking the geometry of the incandescent lamp into consideration, that the centre of the coil 202 of the incandescent lamp lies on the axis of the coupling bore 150 of the adapter part 112. In order to deflect the light emitted by the coil 202 onto the axis of the coupling bore 150, a prism 204 is inserted into the end of the contact-carrier bore 146.

At the same time the base part of the handpiece according to FIG. 22 is modified in such a way that the front face of the light guide 188 is located in the front face of the supply connection piece 70.

In the case of the embodiment example according to FIG. 27 a light-guide holder 206 that bears a monobloc light guide 208 is inserted into the contact-carrier bore 146. The adapter part shown in FIG. 26 is positioned in such a way when it is fitted together with the coupling piece borne by the supply cable that the exterior front face of the light guide 208 is located opposite the front face of a light guide that is contained in the supply cable and that leads to an external light source.

It will be appreciated that the two adapter parts 212 shown in FIGS. 26 and 27 can be exchanged for one another and can cooperate with the same handpieces.

The components of the handpieces described above are made of metal, where possible of high-quality alloy steel, with the exception of the lamp carrier 46, the connector part 40 and the other contact carriers mentioned above.

For the latter, use is made of a plastic material that is stable under the conditions necessary for sterilisation by superheated steam and for cold sterilisation (disinfectant).

I claim:

1. A dental hand-piece comprising a light-providing front portion, a rear portion connectable to a supply cable, a housing, a light source carrier detachably connected mechanically and electrically to the housing, and a light source, arranged on the light source carrier, wherein the light source carrier is formed with a light source receiving receptacle that is open at least in one direction and in which the light source is arranged, and a reflecting surface is arranged at a part of the light source that faces material that does not transmit light so that a corresponding part of the light source is shaded, and the reflecting surface extends over the entire shaded part of the light source.

2. A handpiece as claimed in claim 1, wherein the reflecting surface comprises a layer of material of the group consisting of metallic material and dielectric material that has been deposited by vaporization onto an outer surface of the light source.

3. A handpiece as claimed in claim, 1, wherein the reflecting surface comprises material that is resistant to desinfectant.

4. A handpiece as claimed in claim 1, wherein the reflecting surface carries a protective layer, comprising material that is resistant to disinfectant.

5. A handpiece as claimed in claim 4, wherein the protective layer is formed by glass that has been deposited by vaporization.

6. A handpiece as claimed in claim 1, wherein the reflecting surface is resistant to conditions for sterilization by superheated steam.

7. A handpiece as claimed in claim 1, wherein the reflecting surface carries a protective layer that is resistant to conditions for sterilization by superheated steam.

8. A handpiece as claimed in claim 1, wherein the reflecting surface carries a protective glass layer that has been deposited by vaporization and is resistant to conditions for sterilization by superheated steam.

9. A handpiece as claimed in claim 1, wherein the light source carrier matingly engages a light source carrier receiving receptacle.

10. A handpiece as claimed in claim 9, wherein the light source carrier receiving receptacle is at least partly cylindrical.

11. A handpiece as claimed in claim 10, in which one wall of the light source carrier receiving receptacle has a peripheral extent of approximately 190° to 300° so that two free axial longitudinal edges thereof form a gripping slot.

12. A handpiece as claimed in claim 11, in which said peripheral extent is in the range of approximately 210° to 270°.

13. A handpiece as claimed in claim 11, wherein the light source carrier comprises a gripping means adjacent to the gripping slot.

14. A handpiece as claimed in claim 13, wherein the gripping means is a gripping groove that passes through to a rear front face of the light source carrier.

15. A handpiece as claimed in claim 1, wherein the light source carrier comprises contact parts that cooperate in elastical frictional engagement with complementary contact parts that are carried by the housing.

16. A handpiece as claimed in claim 15, wherein the housing comprises a base-part housing and an operating-part housing that is detachably carried by said base-part housing and wherein a light source carrier receiving receptacle is formed at an end of a projecting shoe section of the base-part housing that overlaps the operating-part housing in the axial direction by a distance that is chosen so as to ensure that light emerging from the light source carrier fully illuminates the environment if an operating end of a tool that is supported in an operating part of the handpiece, the operating-part housing being part of the operating part of the handpiece.

17. A handpiece as claimed in claim 16, wherein the operating part comprises a sleeve section embracing the shoe section of the base-part housing.

18. A handpiece as claimed in claim 1, in which a drive motor is arranged in the handpiece housing, wherein the handpiece housing comprises a line channel that is located radially outside the drive motor and in which supply lines leading to the light source are installed.

19. A handpiece as claimed in claim 1, wherein the handpiece housing comprises a cylindrical supply connection piece that comprises contact means for current supply of the light source, and wherein the contact means are arranged coaxially with respect to the axis of the supply connection piece.

20. A handpiece as claimed in claim 19, in which the contact means are arranged to be coplanar in a free front face of the supply connection piece.

21. A handpiece as claimed in claim 19, having an adapter part that comprises a cylindrical bore receiving the supply connection piece and comprising contact members cooperating with corresponding contact means that are resiliently biased toward the contact means.

22. A handpiece as claimed in claim 21, wherein the adapter part comprises a contact member carrier that extends in a direction that is inclined with respect to the longitudinal axis of the adapter part.

23. A handpiece as claimed in claim 22, wherein the contact member carrier has the form of a cylindrical rod and is arranged in a contact-carrier bore formed in the adapter part that is inclined with respect to a longitudinal axis of the adapter.

24. A handpiece as claimed in claim 1, wherein a light source carrier receiving receptacle is provided in a rear region of the handpiece housing and wherein a light guide extends from the light source carrier receiving receptacle to a front end of the handpiece housing.

25. A handpiece as claimed in claim 24, wherein the light source carrier receiving receptacle comprises an axial bore that emanates from a rear front face of the handpiece housing.

26. A handpiece as claimed in claim 1, wherein a base-part of the housing comprises two detachable base-part segments located axially in sequence and the two base-part segments comprise electrical connecting parts.

27. A handpiece as claimed in claim 26, in which one of said electrical connecting parts is in prestressed engagement with the other electrical connecting part by spring tension.

28. A handpiece as claimed in claim 27, wherein the electrical connecting part carried by a rear one of said base-part segments carries axially projecting spacing means and the electrical connecting part carried by a front one of said base-part segments comprises a recess with which the spacing means can engage.

29. A handpiece as claimed in claim 1 being a straight handpiece with a plurality of axial receptacles for light source carriers emanating from a free front face of the handpiece.

30. A handpiece as claimed in claim 29, in which the axial receptacles are evenly distributed in peripheral direction and each receive a light source carrier with an associated light source.

31. A handpiece as claimed in claim 29, wherein supply lines separated by the light source carriers are guided to connecting pins located at a rear end of the handpiece housing.

32. A handpiece a claimed in claim 31, having means for mutually independent adjustment of currents that flow through various light sources.

33. A handpiece as claimed in claim 32, in which the magnitude of the currents is continuously adjustable.

* * * * *